United States Patent
Peuker et al.

(10) Patent No.: US 9,265,594 B2
(45) Date of Patent: Feb. 23, 2016

(54) DISPENSING DEVICE FOR A DENTAL SUBSTANCE AND METHOD OF MAKING SUCH A DEVICE

(75) Inventors: Marc Peuker, Schondorf (DE); Andreas Boehm, Reichling (DE)

(73) Assignee: 3M Innovative Properties Company, St. Paul, MN (US)

(*) Notice: Subject to any disclaimer, the term of this patent is extended or adjusted under 35 U.S.C. 154(b) by 38 days.

(21) Appl. No.: 13/885,172

(22) PCT Filed: Dec. 12, 2011

(86) PCT No.: PCT/US2011/064375
§ 371 (c)(1),
(2), (4) Date: May 14, 2013

(87) PCT Pub. No.: WO2012/087631
PCT Pub. Date: Jun. 28, 2012

(65) Prior Publication Data
US 2013/0260335 A1    Oct. 3, 2013

(30) Foreign Application Priority Data

Dec. 22, 2010   (EP) .................................... 10196464

(51) Int. Cl.
*B29C 45/14*     (2006.01)
*A61C 19/06*     (2006.01)
(Continued)

(52) U.S. Cl.
CPC .............. *A61C 19/063* (2013.01); *A61C 5/062* (2013.01); *B29C 45/14221* (2013.01); *B29C 45/14336* (2013.01); *B29C 45/14065* (2013.01); *B29L 2031/7506* (2013.01)

(58) Field of Classification Search
CPC ........................................................ B29C 45/14
USPC .................................................. 264/259, 229
See application file for complete search history.

(56) References Cited

U.S. PATENT DOCUMENTS

| 1,621,801 A | 3/1927 | Miller |
| 2,347,737 A | 5/1944 | Fuller |

(Continued)

FOREIGN PATENT DOCUMENTS

| WO | WO 2005/016783 | 2/2005 |
| WO | WO 2006/005206 | 1/2006 |

(Continued)

OTHER PUBLICATIONS

1507 Extended EP Search Report for EP10196464, PCT/US2011/064375, dated Jun. 7, 2011, 6 pages.

(Continued)

*Primary Examiner* — Christina Johnson
*Assistant Examiner* — Xue Liu (57) ABSTRACT

This disclosure is directed, inter alia, a method of making a dispensing device for dispensing a substance comprising a step of providing a mold having a mold space for receiving a solidifyable material. The method further comprises steps of providing a valve member having a first portion formed between first and second areas of an outer surface of the valve member; placing the valve member into the mold space such that at the first area is isolated from the mold space and at least part of the second area is within the mold space; displacing the first portion at least partially relative to another portion of the valve member; and solidifying the material in the mold space and thereby fixing the displaced first portion in place. In one embodiment, the method helps minimizing manufacturing costs and maximizing shelf life of a device filled with substance.

14 Claims, 4 Drawing Sheets

(51) Int. Cl.
*A61C 5/06* (2006.01)
*B29L 31/00* (2006.01)

(56) References Cited

U.S. PATENT DOCUMENTS

2006/0043121 A1* 3/2006 Belanger .................. 222/387
2008/0287880 A1 11/2008 Keller

FOREIGN PATENT DOCUMENTS

WO    WO 2007/104037    9/2007
WO    WO 2010/123800    10/2010

OTHER PUBLICATIONS

International Search Report for PCT International Application No. PCT/US2011/064375, mailed on Apr. 2, 2012, 4 pages.

* cited by examiner

DISPENSING DEVICE FOR A DENTAL SUBSTANCE AND METHOD OF MAKING SUCH A DEVICE

CROSS REFERENCE TO RELATED APPLICATIONS

This application is a national stage filing under 35 U.S.C. 371 of International PCT/US2011/064375, filed Dec. 12, 2011, which claims priority to European Application No. EP 10196464.1, filed Dec. 22, 1010. The disclosures of both applications are incorporated by reference in their entirety herein.

FIELD OF THE INVENTION

The invention relates to a dispensing device for a dental substance and to a method of making the device. The dispensing device has a valve member and may be switched between a storage mode and a use mode. The device is preferably adapted to hermetically encapsulate at least one component of the dental substance during storage.

BACKGROUND OF THE INVENTION

Dental substances are often provided in dispensing devices which allow for storing of the substances over a time, but also enable the substances to be dispensed directly from such devices. Such dispensing devices are often designed for single use and thus typically disposed after. Therefore there are devices which are entirely pouched for storing of the dental substances. Such devices are typically only removed from the pouch directly before use. Other devices are designed for multiuse, and accordingly may contain a sufficient amount of substance for two or more uses. Some of such multiuse devices have an openable closure which enables to reclose the device between two uses.

For example WO 2010/123800 discloses a dispensing device for a dental substance which has an outlet for the dental substance, and a valve for opening and closing the outlet. The device is switchable between a storage mode and an operative mode. In the storage mode a cannula is locked in the device and the valve opens the outlet, and in the storage mode the cannula can be released from the device and the valve closes the outlet.

Although there is a variety of dispensing devices for dental substances there is still a desire for a device which is reusable, but which also provides a maximized shelf life for the substance contained therein after initial use. Further such a device is desirably inexpensive and easy to use.

SUMMARY OF THE INVENTION

The invention in one aspect relates to a method of making a dispensing device for dispensing a substance, in particular a dental substance. The method comprises the steps of:
  providing a mold which is adapted to form a mold space for receiving a solidifyable material;
  providing a valve member having a first portion formed between first and second areas of an outer surface of the valve member;
  placing the valve member into the mold space such that the first area is isolated from the mold space and at least part of the second area is within the mold space;
  displacing the first portion of the valve member at least partially relative to another portion of the valve member and thereby applying a pre-load on the first portion;
  solidifying the material in the mold space and thereby fixing the displaced first portion in place under the pre-load; and
  providing the flowable material in the mold space.

The invention is advantageous in that it preferably provides for manufacturing of a device for dispensing material which allows a substance to be stored over a maximized time period. Such a device may particularly be capable of hermetically encapsulating a substance stored under different temperature and pressure conditions, as they occur for example during transportation of the device from the manufacturing site to a user. Further the invention may help reducing manufacturing costs, for example may minimize costs for assembly of the valve member in the device.

An isolation of a surface area (for example the first area) from the mold space may be achieved by avoiding direct contact of that surface area with the mold space. For example the surface area may be covered by a mold component. Further a surface area may be regarded as being within the mold space if that surface area forms at least part of a boundary of the mold space. For example the surface area may be exposed to the mold space.

In one embodiment the method comprises the step of displacing the first portion together with the first and second areas of the valve member relative to another portion of the valve member. Thus the first portion, or part of the first portion, may be predominantly displaced as a whole rather than compressed as such. The first portion may be partially displaced together with the first and second areas of the valve member relative to another portion of the valve member. For example the first portion may be connected with the remainder of the valve member at a transition region, and the valve member may be deflected so that it is more displaced in a region further remote from the transition region than towards the transition region itself. In one example the first portion is a membrane which is circumferentially connected to the remainder of the valve member. The membrane preferably has a smaller thickness than the portion of the valve member to which the membrane is connected in the same dimensions. The first portion may be displaced in a direction from the second area toward the first area.

In a further embodiment the first and second areas of an outer surface of the valve member are arranged opposite of each other. For example the first and second areas may face away from each other.

In one embodiment the flowable material is injected or pressed in the mold space. The step of providing the flowable material in the mold space may cause the first portion to displace.

In another embodiment the method comprises the step of urging at least one of the valve member and a mold component toward the other one of the valve member and the mold component and thereby causing the first portion to displace. For example the mold component may be urged toward the valve member, particularly to the first portion, and thereby the first portion may be caused to displace. Thereby at least part of the second area may be within the mold space and the remaining part may be outside of the mold space. For example the remaining part of the second area may be covered by the mold component (for example with a mold core). The mold component may further be movable relative to other mold components and used to displace the first portion. Thus a well controlled displacement of the first portion may be achieved.

In one embodiment the method further comprises the step of supporting the valve member in the mold, and suspending support at the first area. For example the valve member may be held in place by a mold component which also seals the first area from the mold space. In an embodiment the valve member has a blind hole defined by an interior wall and an end wall forming the first area. The method may comprise the step of inserting a mold core in the blind hole to support the valve member, but with leaving a space between the first area and the mold core. Thus the valve member may be securely held in place and the first area may be effectively sealed from the mold space. Further thus the first area may be spaced from any mold component enabling the first portion to be displaced into that space.

In one embodiment the method further comprises the step of displacing a second portion of the valve member relative to another portion of the valve member. Thereby the other portion of the valve member may not comprise the first portion. The second portion may be formed between third and fourth areas of the outer valve surface. Thus the valve member may have the first and the second portions which preferably are configured generally identical relative to each other. Further all embodiments described in relation to the first portion only are considered possible embodiments for the first and second portions as well as for only the second portion. A valve member having the first and second portions may be used in combination with a device for dispensing a substance from two individually stored components of the substance. The skilled person will recognize that further embodiments of the device may comprise a valve member having more than two displaceable portions, for example for making devices for dispensing a substance from more than two individually stored components of the substance.

The term "another portion" of the valve member for the purpose of this specification may correspond to a portion of the valve member other than the first and second portions, and particularly a portion adjacent the first or second portions. Such another portion may for example correspond to a part or the remainder of the valve member not including the first and second portions.

In a further aspect the invention relates to a device for dispensing a substance. The device comprises:
 a cartridge;
 a valve member having a first portion formed between first and second areas of an outer surface of the valve member;
 the valve member being accommodated within the cartridge such that the first area is in non-direct contact relationship with the cartridge and at least part of the second area is in direct contact with the cartridge;
 the first portion of the valve member being under pre-load which prevents the first portion from displacing relative to another portion of the valve member; and
 wherein the first portion is fixed in place under pre-load by the cartridge.

Thus a device of the invention may be generally characterized by being made using the method of the invention.

In one embodiment the cartridge is monolithically formed and encases the valve member such that the valve member and the cartridge are non-detachably interlocked with one another.

In a further embodiment the device has at least one chamber. The chamber preferably has an outlet which is openably closed by at least part of the first portion. In particular the device may have a longitudinal axis parallel to which or along the at least one chamber extends. The chamber may extend between a front end and an opposite rear end of the chamber and may open into the outlet. Thus the outlet is arranged adjacent the front end. The chamber may extend with a generally uniform cross-section, for example may be formed by a generally cylindrical chamber wall. Further the chamber is preferably adapted to receive a piston through the rear end which is movable within the chamber in a direction between the front and rear ends of the chamber. Preferably the valve member with the first portion openably closes the outlet. In particular a part of the second surface may block the outlet and the remaining part of the second surface may surround the outlet. The remaining part of the second surface may urge toward the cartridge due to a pre-load provided to the first portion. Thus the first portion may exert a sealing force to the cartridge. This preferably helps maximizing the seal between the cartridge and the valve member. Further this may provide for a maximized shelf life of the device filled with the substance.

In one embodiment the device is adapted such that the valve member is movable generally laterally to the longitudinal axis for opening the outlet. The valve member may for example be rotatable about a rotation axis that is oriented parallel to or in line with the longitudinal axis. The valve member may have a generally cylindrical shape and may comprise a blind hole extending from a first cylinder end face into the valve member. The first area is preferably formed by an end face of the blind hole, and the second area is formed by a second cylinder end face. The first portion thus is preferably formed between the first and second areas. Further the first and second areas are preferably opposing areas which face away from one another.

In one embodiment the second area has a raised portion. The raised portion may protrude from the second cylinder end face. Such raised portion may form a sealing pad. The sealing pad may have a cross-sectional shape which generally corresponds to the cross-sectional shape of the outlet. Therefore the sealing pad may mate with the outlet in the closed position of the valve member. Thus the seal between the valve member and the cartridge may be further maximized.

In a further embodiment the blind-hole is formed at least by a stepped interior wall of a generally cylindrical shape and the first area. For example the first area may form the end face of the blind hole. Further the blind-hole may extent into the valve member with a first diameter, and may continue towards the first area with a smaller second diameter. Thus for molding the cartridge the valve member may be held by a mold component penetrating into the blind hole. Further this mold component may be prevented from getting into contact with the first area by the step formed within the blind-hole.

In one embodiment the device has two chambers for holding components of a substance. Each of the chambers preferably has an outlet which is openably closed by the valve member. The valve member is preferably movable relative to both outlets for opening the outlets. Further the device may have at least one plunger for extruding the substance from the chambers through the outlets. The plunger may have a piston which seals the chamber at their rear ends. Embodiments described with regard to a chamber, an outlet and a first portion therefore are not limited to one chamber, one outlet and one portion only.

Therefore in another embodiment the device comprises:
 a cartridge;
 a valve member having a first portion formed between first and second areas of an outer surface of the valve member and a second portion formed between third and fourth areas of the outer surface of the valve member;
 the valve member being accommodated within the cartridge such that the first and third areas are in non-direct contact relationship with the cartridge and at least part of the second and fourth areas are in direct contact with the cartridge;

the first and second portions of the valve member being under pre-load and urging toward the cartridge to a greater extent than another portion of the valve member; and the cartridge fixes the pre-loaded first and second portions in place.

The device may have two chambers each having an outlet which is openably closed by at least part of the first and second portions, respectively. Each chamber may extend between a front and a rear end parallel to the longitudinal axis of the cartridge. Each of the outlets may be arranged adjacent the front end of the respective chamber. The valve member may have a generally cylindrical shape with two blind-holes extending from a first cylinder end face into the valve member. The first and third areas may be formed by end faces of the blind-hole, and the second and fourth areas may be formed by a second cylinder end face. Further the second and fourth areas each may have a raised portion protruding from the second cylinder end face. Each of the blind-hole may be formed at least by a stepped interior wall of a generally cylindrical shape and the first or third area respectively.

DETAILED DESCRIPTION OF THE INVENTION

Figures 1, 2, 3:
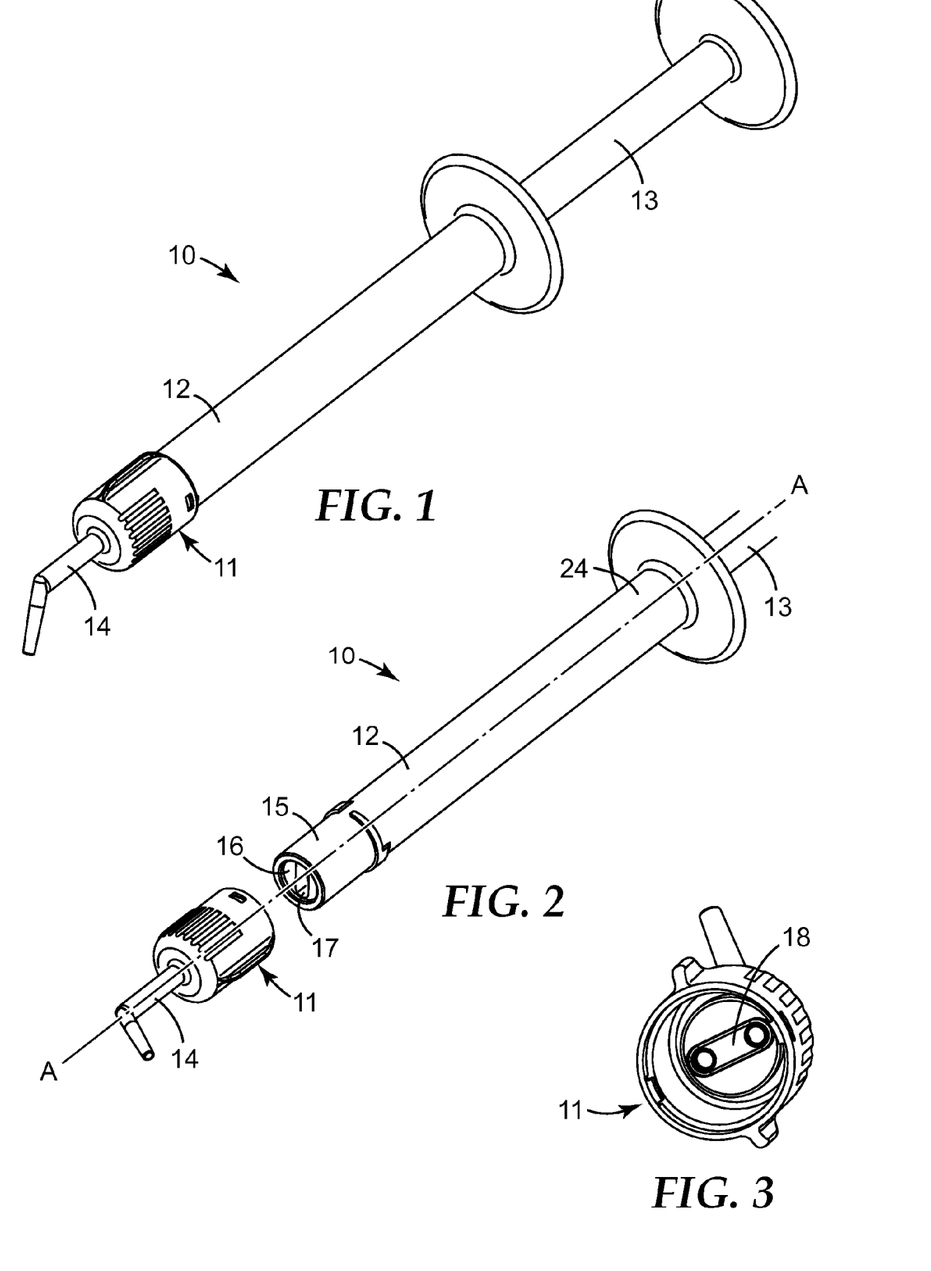
FIG. 1 is a perspective view of a dispensing device according to an embodiment of the invention.
FIG. 2 is a perspective view illustrating details of the dispensing device shown in FIG. 1.
FIG. 3 is a perspective view of further details of the dispensing device shown in FIG. 1.

FIG. 1 illustrates a dispensing device 10 for a dental substance. The device 10 has a nozzle appliance 11, a cartridge 12 and a plunger 13. The device 10 may contain two components of the dental substance separately stored in chambers (not shown in this Figure) in the cartridge 12. The components may be merged within a nozzle 14 of the nozzle appliance 11 as the plunger 13 is pushed into the cartridge 12. The nozzle 14 may contain a static mixer for mixing the two components before they are dispensed from the nozzle 14. The device 10 may be pre-filled with an amount of substance sufficient for multiple uses, for example already at a manufacturing stage of the device 10. Further the device 10 is preferably adapted to hermetically encapsulate the components in the cartridge 12. Therefore the dispensing device 10 preferably allows for storing of the substance over several months or years and for maintaining the desired properties of the substance in essence over such periods of time.

FIG. 2 shows the device 10 with the nozzle appliance 11 detached from the cartridge 12 for the purpose of explanation. The nozzle appliance and the cartridge may in certain embodiments be detachable, but in other embodiments unreleasably interlocked with one another. The cartridge 12 has a front end 15 which accommodates a valve member 16. The valve member 16 is rotatable about a longitudinal axis A between an open position in which the device 10 can be used for dispensing the substance and a closed position in which the device 10 encapsulates the substance for storage. Preferably the device is adapted such that it can be reopened and reclosed multiple times. The valve member has a channel 17 which in the open position connects outlets (not shown) for the components with the nozzle 14 of the nozzle appliance 11. Thus in the open position the valve member enables the components to flow from the cartridge 12 through the valve member 16 toward the nozzle 14. Further the valve member 16 seals the outlets in the closed position. Therefore the valve member seals the front end 15 of the cartridge in the closed position. The cartridge 12 at a rear end 24 receives the plunger 13. Preferably the plunger 13 is adapted to seal the cartridge 12 at the rear end.

FIG. 3 shows an interior of the nozzle appliance 11. In particular the nozzle appliance 11 comprises a first engagement member 18. The first engagement member 18 is adapted to engage the channel 17 (FIG. 2) of the valve member in an assembled stage of the nozzle appliance 11 and the cartridge. However in other examples the valve member may have a second engagement member in addition to the channel 17, and the first and second engagement members may be adapted for mating and engaging with one another in an assembled stage of the nozzle appliance 11 and the cartridge 12. The first engagement member 18 preferably provides for an anti-twist connection between the nozzle-appliance 11 and the valve member 16. Therefore a rotation of the nozzle appliance 11 relative to the cartridge 12 preferably also causes the valve member 16 and the cartridge 12 to rotate relative to each other. Thus the device may be conveniently opened and closed by rotating the nozzle appliance 11 and the cartridge 12 relative to one another.

Figure 4:
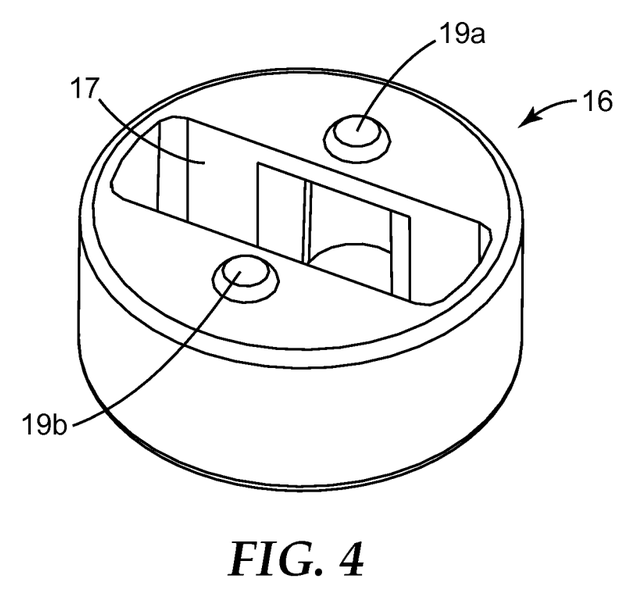
FIG. 4 is a perspective view of a valve member according to an embodiment of the invention.

FIG. 4 shows the valve member 16 in more detail. The channel 17 has a non-circular cross-section. Therefore the channel 17 is adapted for being engaged for rotation of the valve member 16. In particular the first engagement member 18 of the nozzle appliance 11 and the channel 17 may have similar cross-sectional shapes, for example rectangular, triangular or any other polygonal or non-circular shapes. The valve member 16 further has first and second sealing pads 19a, 19b for sealing with outlets of the cartridge 12 as illustrated in FIG. 5.

Figure 5:
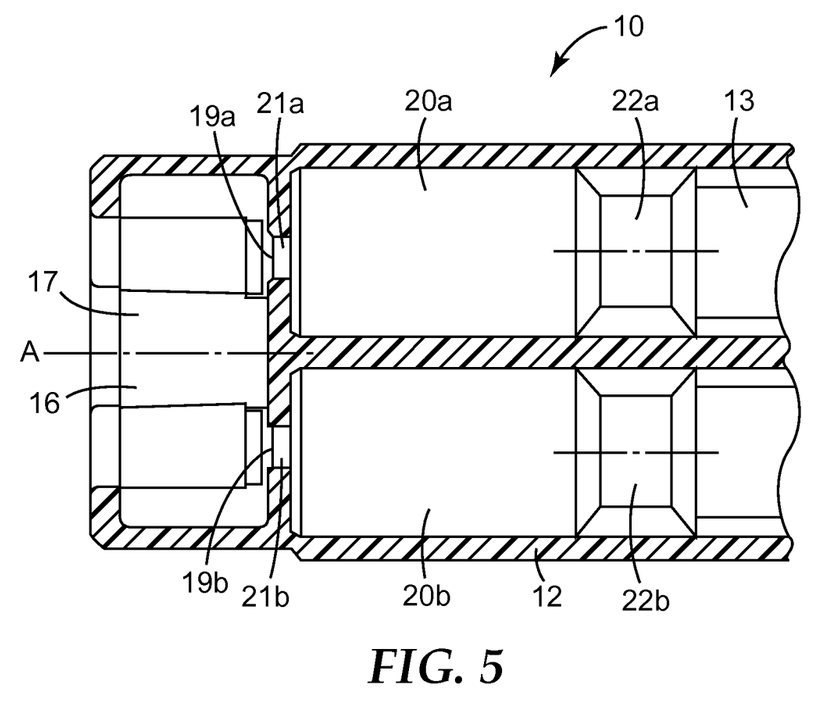
FIG. 5 is a partial cross-sectional view of the dispensing device according to a further embodiment of the invention.

FIG. 5 shows a cross-section of the cartridge 12 of the device 10. The cartridge 12 has a first and a second chamber 20a, 20b. Each of the first and second chambers 20a, 20b may contain a component of the dental substance. Further the first and second chambers 20a, 20b at front ends have first and second outlets 21a, 21b, respectively. The first and second outlets 21a, 21b are closed by the first and second sealing pads 19a, 19b of the valve member 16. The first and second chambers 20a, 20b at rear ends are closed by first and second pistons 22a, 22b which are movably and sealingly arranged within the first and second chambers 20a, 20b, respectively. The first and second pistons 22a, 22b may be part of the plunger 13, for example may be formed monolithically with the plunger 13. Further the first and second pistons 22a, 22b and the plunger 13 may be separate parts. The situation shown corresponds to the closed position of the valve member and the cartridge relative to each other. The device may be brought in the open position by rotating the valve by about 90 degrees about the longitudinal axis A (not shown). In the open position the channel 17 connects to the first and second outlets 21a, 21b (also not shown).

Figure 6:
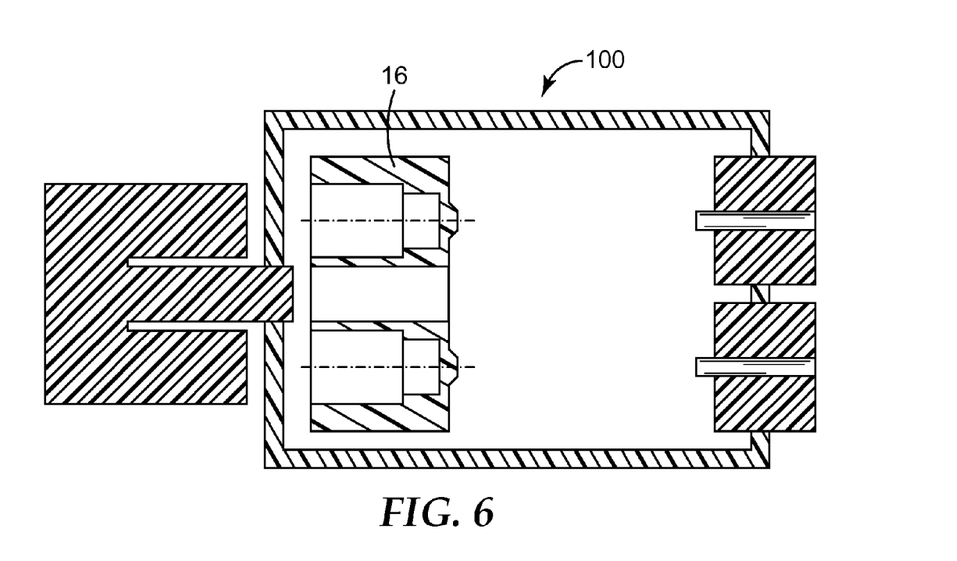
FIGS. 6-8 are schematic cross-sectional views illustrating a molding process according to a further embodiment of the invention.

FIG. 6 shows a mold 100 in which a pre-manufactured valve member 16 is placed. The mold 100 is adapted for molding a cartridge around the valve member 16. Therefore the mold 100 is further adapted to receive a solidifyable material. For example the mold may be suitable for injection molding the cartridge from a molten plastic material and the plastic material may be of a type being generally solid at about room temperature. Possible plastic materials comprise polypropylene, polyoxymethylene, polycarbonate, polyamide, polybutadiene terephthalate, polyethylene terephthalate or rubber for example.

Figure 7:
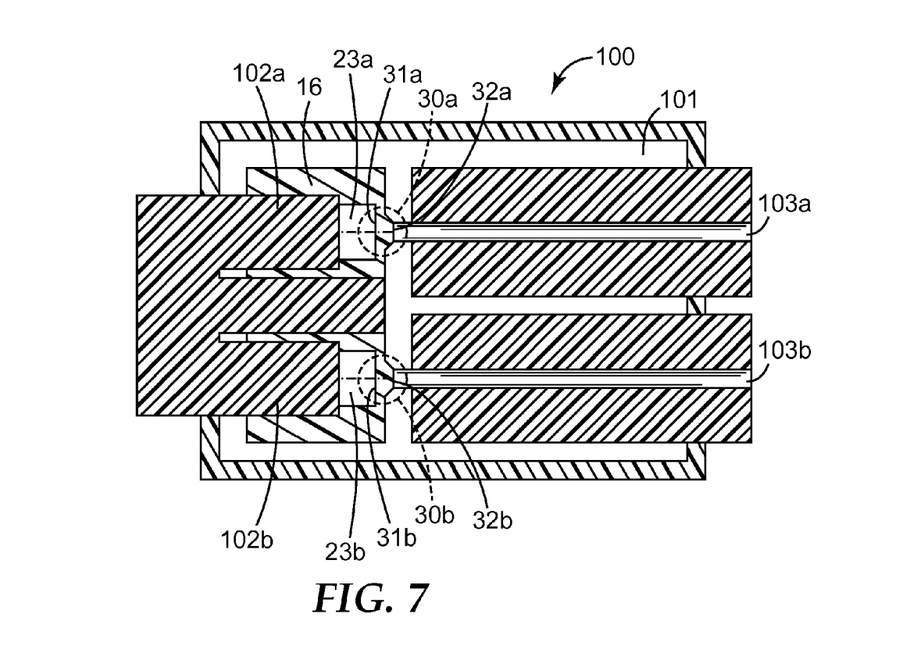

FIG. 7 shows the mold 100 with all mold components and the valve member 16 positioned ready for molding. A mold space 101, which is the space to be filled by the solidifyable material, is thus formed within the mold 100. The valve member 16 has a first portion 30a formed between a first area 31a and a second area 32a. The first and second areas 31a, 32a are part of an overall outer surface of the valve member 16. The valve member 16 is placed in the mold space 101 such that the first area 31a is isolated from the mold space 101. This is achieved by a first front core 102a extending in and thus sealing a first blind-hole 23a of the valve member 16 which is partially formed by the first area 31a. In particular the first area 31a is formed by an end wall of the first blind-hole 23a. Further the first blind-hole 23a has a stepped cross-section over its depth. The stepped configuration prevents the first front core 102a to entirely penetrate the first blind-hole 23a. Accordingly the first area 31a is spaced from the core 102a and thus not supported. The second area 32a is located partially within the mold space 101 and partially covered by a front face of a first rear core 103a. The covered area of the second area 32a is therefore also located outside the mold space because material provided in the mold space is prevented from getting into contact with the covered area within the second area 32a. The valve member 16 in this example further has at least a second portion 30b formed between a third area 31b and a fourth area 32b. Part of the fourth area 32b is covered by a second rear core 103b, and a second front core 102b is placed within a second blind-hole 23b. The second portion 30b, the third and the fourth area 31b, 32b are preferably configured substantially identical to the first portion 30a with the first and second areas 31a, 32a, respectively. Further the second front and rear cores 102b, 103b are configured and arranged generally identical to the configuration and arrangement of the first front and rear cores 102a, 103a respectively. The second blind-hole 23b further generally corresponds in configuration to the first blind-hole 23a.

Figure 8:
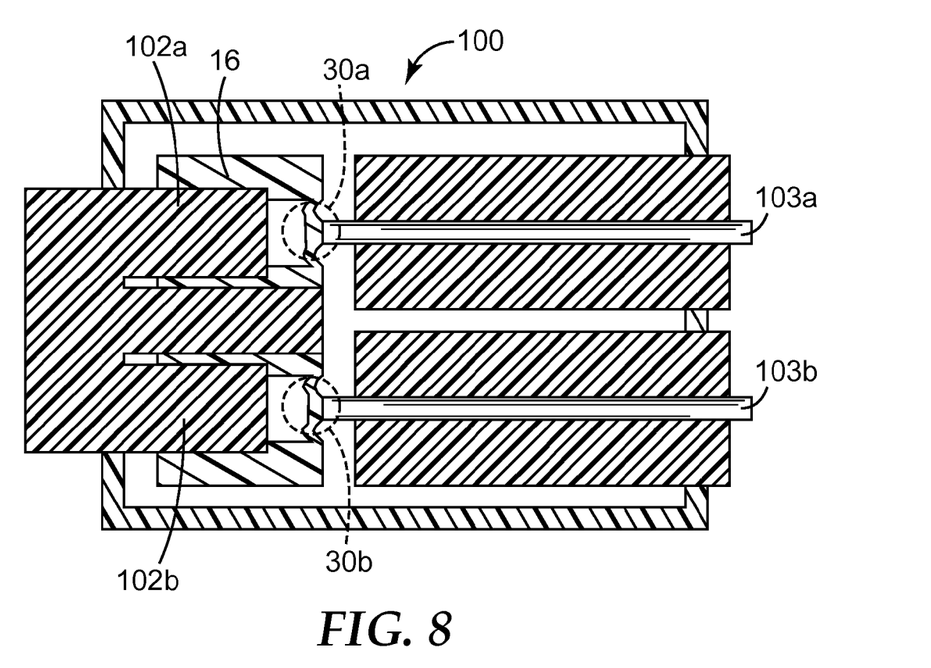

FIG. 8 shows the first and second rear cores 103a, 103b placed further toward the valve member 16. As a result the first portion 30a and the second portion 30b of the valve member 16 are displaced relative to the remainder of the valve member 16. Preferably the displacement corresponds to a resilient displacement. This may be provided for example by the valve member 16 being generally elastic. For example the valve member 16 may be made of polyoxymethylene, polycarbonate, polyamide, polybutadiene terephthalate, polyethylene terephthalate or rubber.

In a not shown embodiment the first and second portions 30a, 30b may be supported by the front cores 102a, 102b in the displaced position, for example fixedly held between the front cores 102a, 102b and the rear cores 103a, 103b, respectively. In the position shown the mold 100 may be filled with a solidifyable material so that also the valve member 16 is embedded in the material. The solidified material preferably fixes or freezes the displaced first and second portions 30a, 30b in place under pre-load as shown in FIG. 9.

Figure 9:
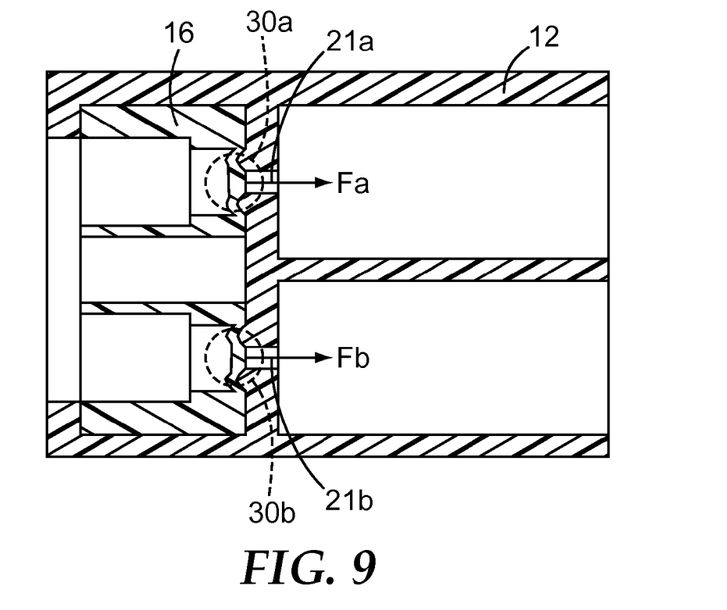
FIG. 9 is a cross-sectional view of a dispensing device obtained from the process illustrated in FIGS. 6-8.

FIG. 9 shows the cartridge 12 as it may be molded using a mold as shown in FIGS. 6-7. The cartridge has outlets 21a, 21b which are sealed by the valve member 16. In the example the valve member is over-molded by solidified material. In particular the valve member in this example is unreleasably enclosed within the cartridge 12. The first and second portions 30a, 30b exert sealing forces Fa, Fb toward the first and second outlets 21a, 21b, respectively. The sealing forces preferably result from reset forces of the first and second portions 30a, 30b which are enclosed within the cartridge 12 under pre-load. Such pre-load is preferably generally reestablished or maintained after opening and reclosing the cartridge, for example by rotating the valve member about the longitudinal axis A.

The skilled person will recognize that the invention is not limited to a device for dispensing a substance obtained from two components, but that the invention can likewise be used for a single component device or a device for more than two components.

The invention claimed is:

1. A method of making a dispensing device for dispensing a substance, comprising:
   providing a mold adapted to form a mold space for receiving a solidifyable material;
   providing a valve member having a first portion formed between first and second areas of an outer surface of the valve member;
   placing the valve member into the mold space such that the first area is isolated from the mold space and at least part of the second area is within the mold space;
   displacing the first portion of the valve member at least partially relative to another portion of the valve member;
   providing the solidifyable material in the mold space; and
   solidifying the material in the mold space and thereby fixing the displaced first portion in place.

2. The method of claim 1, further comprising pressing the solidifyable material in the mold space and thereby causing the first portion to displace.

3. The method of claim 1, further comprising urging at least one of the valve member and a mold component toward the other one of the valve member and the mold component and thereby causing the first portion to displace.

4. The method of claim 1, further comprising supporting the valve member in the mold and suspending support at the first area.

5. The method of claim 4, wherein the valve member has a blind hole defined by an interior wall and an end wall forming the first area, and further comprising inserting a mold core in the blind hole to support the valve member while leaving a space between the first area and the mold core.

6. The method of claim 1, further comprising displacing a second portion of the valve member relative to another portion of the valve member, wherein the second portion is formed between third and fourth areas of the outer valve surface.

7. A method of making a dispensing device for dispensing a substance, comprising:
   providing a mold adapted to form a mold space for receiving a solidifyable material;
   providing a valve member having a first portion formed between first and second areas of an outer surface of the valve member;
   placing the valve member into the mold space such that a first area is isolated from the mold space and at least part of the second area is within the mold space;
   displacing the first portion of the valve member at least partially relative to another portion of the valve member;
   solidifying the material in the mold space and thereby fixing the displaced first portion in place; and
   pressing the solidifyable material in the mold space and thereby causing the first portion to displace.

8. The method of claim 7, further comprising supporting the valve member in the mold and suspending support at the first area.

9. The method of claim 8, wherein the valve member has a blind hole defined by an interior wall and an end wall forming the first area, and further comprising inserting a mold core in the blind hole to support the valve member while leaving a space between the first area and the mold core.

10. The method of claim 7, further comprising displacing a second portion of the valve member relative to another portion of the valve member, wherein the second portion is formed between third and fourth areas of the outer valve surface.

11. A method of making a dispensing device for dispensing a substance, comprising:
   providing a mold adapted to form a mold space for receiving a solidifyable material;
   providing a valve member having a first portion formed between first and second areas of an outer surface of the valve member;
   placing the valve member into the mold space such that a first area is isolated from the mold space and at least part of the second area is within the mold space;
   displacing the first portion of the valve member at least partially relative to another portion of the valve member;
   solidifying the material in the mold space and thereby fixing the displaced first portion in place; and
   urging at least one of the valve member and a mold component toward the other one of the valve member and the mold component and thereby causing the first portion to displace.

12. The method of claim 11, further comprising supporting the valve member in the mold and suspending support at the first area.

13. The method of claim 12, wherein the valve member has a blind hole defined by an interior wall and an end wall forming the first area, and further comprising inserting a mold core in the blind hole to support the valve member while leaving a space between the first area and the mold core.

14. The method of claim 11, further comprising displacing a second portion of the valve member relative to another portion of the valve member, wherein the second portion is formed between third and fourth areas of the outer valve surface.

* * * * *